United States Patent [19]

Honda et al.

[11] Patent Number: 5,279,820

[45] Date of Patent: Jan. 18, 1994

[54] TERMITICIDES

[75] Inventors: Yoshitaka Honda; Norio Yanagisawa, both of Osaka, Japan

[73] Assignee: Daikin Industries, Ltd., Osaka, Japan

[21] Appl. No.: 613,074

[22] Filed: Nov. 15, 1990

[30] Foreign Application Priority Data

Nov. 15, 1989 [JP] Japan ................... 1-297998

[51] Int. Cl.$^5$ ............................................ A01N 31/00
[52] U.S. Cl. ...................... 424/78.08; 424/410; 424/DIG. 11; 424/601
[58] Field of Search .............. 514/723, 759; 424/78, 424/DIG. 11, 78, 78.08, 410, 601

[56] References Cited

U.S. PATENT DOCUMENTS

| | | | |
|---|---|---|---|
| 2,732,398 | 1/1956 | Brice et al. | 562/30 |
| 4,092,110 | 5/1978 | Adolphi et al. | 424/DIG. 11 |
| 4,438,593 | 3/1984 | McNew et al. | 424/80 |
| 4,467,013 | 8/1984 | Baldwin | 428/421 |
| 4,582,901 | 4/1986 | Prestwich | 424/78.08 |
| 4,631,302 | 12/1986 | Supcoe | 424/83 |
| 4,803,067 | 2/1989 | Brunetta et al. | 514/723 |

FOREIGN PATENT DOCUMENTS 2342828  9/1977  France.
84/02650  7/1984  World Int. Prop. O.

*Primary Examiner*—Thurman K. Page
*Assistant Examiner*—Peter F. Kulkosky
*Attorney, Agent, or Firm*—Birch, Stewart, Kolasch & Birch

[57] ABSTRACT

A termiticide comprising, as an active ingredient, a polymer which comprises repeating units of the formula:

$$-C_xF_{2x}O-$$

wherein x is an integer of 1 to 4, or the formula:

$$-CX_1X_2CF_2CF_2O-$$

wherein $X_1$ and $X_2$ are the same or different and each a hydrogen atom, a fluorine atom or a chlorine atom, provided that $X_1$ and $X_2$ are not fluorine atoms simultaneously, and has at least one polar group at polymer chain ends, which has no or little toxicity on the human beings or animals and long-lasting termiticidal effects.

13 Claims, No Drawings

TERMITICIDES

BACKGROUND OF THE INVENTION

1. Field of the Invention

The present invention relates to a termiticide comprising a specific fluorine-containing polymer as an active ingredient.

2. Description of the Related Art

Buildings, in particular, wooden buildings increasingly suffer from significant damages caused by termites. Termites damage not only the buildings but also eat synthetic resins or rubbers which cover underground cables, whereby insulation of the cables is deteriorated. It is said that an amount of damages caused by the termites is about one hundred million yen per year in Japan. Therefore, it is very important to control or destroy the termites.

As termiticides, organic chlorine base compounds such as Chlordan, Heptachlor, Dildrin, Aldrin, Linden, chloronaphthalene and the like were widely used, but their use has been forbidden due to their toxicity.

Recently, organic phosphorus base compounds such as Phoxime, Chlorbiliphos, Phention, Phenitrochion, Bilidaphenchion, Tetrachlobinphos, etc. and carbamate type compounds such as Carbaryl, etc. are used.

The organic chlorine base compounds have strong termiticidal activities, but they have toxicity against other organisms including human beings and pollute environments. Some of conventional termiticides may not have such problems but have insufficient termiticidal activities.

Since the termites live in places where their control or destruction is difficult such as in soils below floors or wooden foundations of the buildings, the termiticide is expected to have a termiticidal effect which lasts as long as possible after one application.

SUMMARY OF THE INVENTION

One object of the present invention is to provide a termiticide which has no or little toxicity against organisms except termites.

Another object of the present invention is to provide a termiticide having a long-lasting termiticidal activity.

These and other objects are accomplished by a termiticide comprising, as an active ingredient, a polymer which comprises repeating units of the formula:

$$—C_xF_{2x}O—$$

wherein x is an integer of 1 to 4, or the formula:

$$—CX_1X_2CF_2CF_2O—$$

wherein $X_1$ and $X_2$ are the same or different and each a hydrogen atom, a fluorine atom or a chlorine atom, provided that $X_1$ and $X_2$ are not fluorine atoms simultaneously, and has at least one polar group at polymer chain ends.

The termiticide of the present invention does not kill the termites but prevents damages caused by the termites by imparting a material to be treated with recognition block or repellency by the termites.

DETAILED DESCRIPTION OF THE INVENTION

Among the polymers to be used in the present invention, are preferred a polymer of the formula:

$$X—(C_3F_6O)_l—(C_2F_4O)_m—(CF_2O)_n—(C_2F_4)_p—Y \quad (I)$$

wherein X is a fluorine atom or a group of the formula: $C_qF_{2q+1}O—$ in which q is an integer of 1 to 15; Y is a group of the formula: —COR in which R is a halogen atom, a hydrogen atom or a $C_1$-$C_8$ alkyl or fluoroalkyl group), a group of the formula: —OCOR' or —SO$_2$R' in which R' is a halogen atom or a group of the formula: —NCO; l is a number of 0 to 200; m is a number of 0 to 200, n is a number of 0 to 200; and p is a number of 0 to 200, provided that the sum of l, m and n is not zero, and a polymer of the formula:

$$X—(CX_1X_2CF_2CF_2O)_r—(CX_1X_2CF_2)_n—Y \quad (II)$$

wherein X, $X_1$, $X_2$, Y and n are the same as defined above, and r is a number of 1 to 200.

Herein, —$C_2F_4$— includes —$CF_2CF_2$— and —$CF(CF_3)$—, and —$C_3F_6$— includes —$CF_2CF_2CF_2$— and —$CF(CF_3)$—$CF_2$—.

Specific examples of the polymers (I) to be used in the present invention are as follows:

$$X—(CFCF_2O)_r—(C_2F_4)_p—Y \quad (1)$$
$$\quad\quad |$$
$$\quad CF_3$$

$$X—(CFCF_2O)_r—(CF_2O)_n—(C_2F_4)_p—Y \quad (2)$$
$$\quad\quad |$$
$$\quad CF_3$$

$$X—(CF_2CF_2O)_m—(CF_2O)_n—(C_2F_4)_p—Y \quad (3)$$

$$X—(CF_2CF_2CF_2O)_r—(CF_2O)_n—(C_2F_4)_p—Y \quad (4)$$

wherein X, l m, n and p are the same as defined above, and Y is a polar group as defined below.

A specific example of the polymer (II) is a polymer:

$$X—(CH_2CF_2CF_2)_r—CH_2CF_2—Y \quad (5)$$

In addition, following polymers may be used in the present invention:

$$X—(CH_2CF_2CF_2O)_r—(CFCF_2O)_m—(C_2F_4)_n—Y \quad (6)$$
$$\quad\quad\quad\quad\quad\quad\quad\quad |$$
$$\quad\quad\quad\quad\quad\quad\quad CF_3$$

$$X—(CF_2CF_2CF_2O)_r—(CHFCF_2CF_2O)_m—(C_2F_4)_n—Y \quad (7)$$

The polymer used in the present invention has a polar group at least at one end of the polymer chain, although it may have polar groups at both ends of the polymer chain. Examples of the polymer having the polar groups at both polymer chain ends are $$Y—(OCF_2CF_2CF_2)_l—(C_2F_4)_2—(CF_2CF_2CF_2O)_l—Y \quad (9)$$

$$Y—CF_2CF_2—(OCF_2CF_2CF_2)_l—(OC_6F_{12}O)—(CF_2CF_2CF_2O)_l—CF_2CF_2—Y \quad (10)$$

In general, repeating units such as —$C_xF_{2x}O$— or —$CX_1X_2CF_2CF_2O$— are randomly contained in a single polymer chain.

A molecular weight of the polymer to be used in the present invention is not critical, and is generally from 500 to 200,000, preferably from 2500 to 8000.

The polymers may be used independently or as a mixture of two or more of them.

Specific examples of the polar group are —OH, —SH, —NHR$^3$, —COR$^1$, —COOR$^1$, —SiR$^2_a$R$^4_{3-a}$, —CN, —NCO, —OCO—C(R$^3$)=CH$_2$, —OC(R$^3$)=CH$_2$, —OCF=CF$_2$,

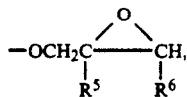

—OSO$_2$CF$_3$, —OCOR$^7$, —OCN, —N(R$^3$)CN, —CO—O—COR$^2$, —N=O, —I, —CH(OCH$_3$)$_2$, —SO$_2$R$^7$, —(OCH$_3$)=NH, —C(NH$_2$)=NH wherein R$^1$ is a hydrogen atom, a halogen atom, a C$_1$-C$_8$ alkyl group, a C$_1$-C$_8$ fluoroalkyl group, a phenyl group or a group of the formula

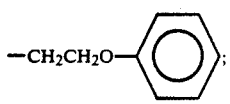

R$^2$ is a C$_1$-C$_8$ alkyl group or a phenyl group; R$^3$ is a hydrogen atom or R$^2$, R$^4$ is a halogen atom or a C$_1$-C$_8$ alkoxy or acyloxy group; a is 1, 2 or 3; R$^5$ and R$^6$ are independently a hydrogen atom or a C$_1$-C$_4$ alkyl group or both alkylene groups which form a 5- or 6-members ring together with the carbon atoms to which they are bonded; and R$^7$ is a halogen atom, —O-COC(CH$_3$)=CH$_2$, —NHCOC(CH$_3$)=CH$_2$, —O-COCH=CH$_2$, —OCH=CH$_2$, OCH$_2$CH=CH$_2$, —NHCH$_2$CH=CH$_2$, —N(CH$_2$CH=CH$_2$)$_2$,

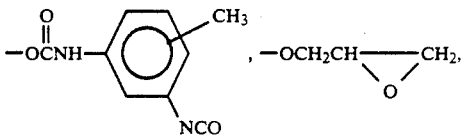

—CH$_2$CH(OH)CH$_2$OCH$_2$CH—CH$_2$.
\\O/

—OCONH(CH$_2$)$_3$Si(OCH$_3$)$_3$, —OCH$_2$CH(OH)C-H$_2$O(CH$_2$)$_3$(OCH$_3$)$_3$, —OCONH(CH$_2$)$_2$OCOC(CH$_3$-)Si(OCH$_3$)$_3$,

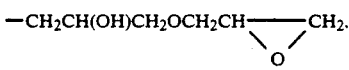

—OCH=CH$_2$, —OCH$_2$CH—CH$_2$.
\\O/

—OCH$_2$CH=CH$_2$, —N(CH$_2$CH$_2$OH)$_2$, —NHCH$_2$CH=CH$_2$, —NH(CH$_2$)$_3$Si(OCH$_3$)$_3$, —N(CH$_2$CH=CH$_2$)$_2$, and —OCH$_2$—CH(OH)C-H$_2$O(CH$_2$)$_3$Si(OCH$_3$)$_3$.

Among the above polar groups, —COR$^1$, —O-COCR$^7$, —SO$_2$R$^7$ and —NCO are preferred, and —COR$^1$ are more preferred.

The specific examples of the polymer which can be used in the present invention may be found in U.S. Pat. No. 4,845,268 the disclosure of which is hereby incorporated by reference.

Although the polymer as such can be used as the termiticide, it is usually used as an oily preparation in an organic solvent or in the form of an emulsion or an aerosol together with an emulsifier, a solubilizing agent, a penetrating agent, a stabilizer, a filler, a binding agent, a propellant and the like. Examples of the organic solvent are trichlorotrifluoroethane, pentafluorodichloropropane, hexafluorotetrachlorobutane, perfluorohexane, tetrahydrofuran (THF), diglyme, triglyme, tetraglyme and the like.

A concentration of the active ingredient in the preparation or a dose of the preparation depend on the form of preparation, an application method, kinds of materials to be treated such as wood or soil, objects (prevention or control), kinds of termites, degrees of damage caused by the termites, and the like.

In general, in case of a liquid or powder preparation, the polymer as the active ingredient s contained in an amount of 0.1 to 20% by weight, more preferably 0.5 to 10% by weight based on the weight of the whole preparation.

The termiticide of the present invention is particularly effective against Reticulitermes speratus Kolbe, Coptotermes formosanus Shiraki and Cryptotermes demesticus Haviland.

According to the present invention, the active ingredient as such or the preparation containing the active ingredient may be applied to places where the termites breed or nest, and to any materials to which termite damage is to be prevented, such as foundations or pillars of buildings, buildings as such, soils around the buildings, water-proof sheets, wrapping materials, coating materials of wires or cables and the like, by coating, spraying, dipping, injecting, spreading, mixing or incorporation therein.

The termiticide of the present invention may be used together with other termiticides depending upon the degree of breeding of the termites and the damage. Since the damage by the termites is often accompanied by wood rot due to wood rotting fungi, it is effective to use the termiticide of the present invention in combination with an antiseptic agent. In addition, an ant-controlling agent can be employed. Specific examples of the ant-controlling agent are organic phosphorus base insecticides (e.g. Phoxime, Chloropiliphos, Brothiophos, Phenitrotion, Tetrachlobinphos, etc.), carbamate type insecticides (e.g. Proboxy, BPMC, Carbaryl, etc.) monochloronaphthalene, bis(2,3,3,3-tetrachloropropyl)ether, and the like. Although the organic chlorine-base insecticides (e.g. Chlordan, Heptachlor, etc.) may be used in combination with the termiticide of the present invention, they should be carefully used since they are accumulated and concentrated in natural environment.

Examples of the antiseptic agent to be compounded in the termiticide of the present invention are Creosote oil, pentachlorophenyl laurate, 2,4,6-tribromophenol, 4-chlorophenyl-3'-iodo-propargylformal, diiodomethyl-4-methylphenylsulfone, N,N-dimethyl-N'-(dichlorofluoromethylthio)-N'-phenylsulfamide, bis(tributyltin) oxide, tributyltin phthalate, an aluminum salt of N-nitroso-N-cyclohexylhydroxylamine, N-cyclohexyl-N-methoxy-2,5-dimethylfuran-3-carbocylic acid amide, and the like. They may be used independently or as a mixture of two or more of them.

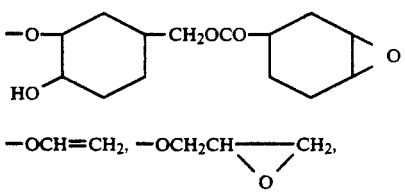

PREFERRED EMBODIMENTS OF THE INVENTION

The present invention will be illustrated by the following Examples, in which "%" is by weight unless otherwise indicated.

EXAMPLE 1

An acid fluoride of the formula:

$$F-(CF_2CF_2CF_2O)_n-CF_2CF_2COF$$

wherein n is 22 on the average was dissolved in trichlorotrifluoroethane (R113) to prepare a solution at a concentration of 0.5%, 1%, 3% or 10%.

In each solution, a small piece (5 mm×5 mm×5 mm) of Japanese larch (*Larix leptolepis*) was dipped for 24 hours. Then, the piece absorbing the solution was placed in a group of 50 termites (*Reticulitermes speratus*) consisting of 45 workers (W) and 5 soldiers (S), and the group was observed for three weeks. The results are shown in Table.

TABLE

| Days | Number of survived termites | | | | Without wood piece (without food) | With untreated wood piece (with food) |
|------|------|------|------|------|------|------|
|      | 10%  | 3%   | 1%   | 0.5% |      |      |
| 1st  | W 45 | W 45 | W 45 | W 45 | W 45 | W 45 |
|      | S 5  | S 5  | S 5  | S 5  | S 5  | S 5  |
| 11th | W 5  | W 4  | W 16 | W 18 | W 40 | W 40 |
|      | S 2  | S 0  | S 1  | S 2  | S 3  | S 4  |
| 12th | W 5  | W 2  | W 5  | W 16 | W 12 | W 40 |
|      | S 0  | S 0  | S 0  | S 1  | S 2  | S 4  |
| 13th | W 4  | W 1  | W 4  | W 10 | W 10 | W 40 |
|      | S 0  | S 0  | S 0  | S 0  | S 0  | S 4  |
| 14th | W 4  | W 1  | W 3  | W 5  | W 8  | W 40 |
|      | S 0  | S 0  | S 0  | S 0  | S 0  | S 4  |
| 15th | W 4  | W 1  | W 0  | W 4  | W 5  | W 30 |
|      | S    | 0    | S 0  | S 0  | S 0  | S 4  |
| 16th | W 3  | W 1  | W 0  | W 2  | W 4  | W 30 |
|      | S 0  | S 0  | S 0  | S 0  | S 0  | S 4  |
| 17th | W 2  | W 0  | W 0  | W 2  | W 2  | W 30 |
|      | S 0  | S 0  | S 0  | S 0  | S 0  | S 4  |
| 18th | W 2  | W 0  | W 0  | W 0  | W 2  | W 30 |
|      | S 0  | S 0  | S 0  | S 0  | S 0  | S 4  |
| 19th | 0    | 0    | 0    | 0    | 0    | W 30 |
|      |      |      |      |      |      | S 4  |

EXAMPLE 2

The solution prepared in Example 1 was coated on a small pine piece by dipping or spraying. Then, the pine piece was dyed with Fantred in red and fed to a group of termites. After two weeks, no eating scar was found on the pine pieces, or no termite was colored red.

For comparison, a pine piece which was dyed with Fantred but was not coated with the termiticide was fed to a group of termites. After two weeks, eating scars were found on the pine piece and the termites were colored red.

EXAMPLE 3

The same experiment as in Example 1 was repeated by using $CF_3CF_2CF_2O[CF(CF_3)-CF_2O]_3-COF$ (A) or $F-(CH_2CF_2CF_2O)_n-CH_2CF_2COF$ (B) in which n is 22 on the average as a polymer. When the polymer (A) was used, all the termites were dead after 8 days, while when the polymer (B) was used, all the termites were dead after 10 days.

From the results that the termites died after the same test period in the case where the wood piece coated with the polymer of the present invention was fed and in the case where the untreated wood piece was fed, and there found no eating scar in Example 2, it is understood that the termites were starved to death and not killed with the polymer of the present invention. The death of the termites is not natural death, since the termites which were fed survived.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A termiticide composition comprising in an effective amount as a termiticidal active ingredient, a polymer which comprises repeating units of the formula:

$$-C_xF_{2x}O-$$

wherein x is an integer of 1 to 4, or the formula:

$$-CX_1X_2CF_2CF_2O-$$

wherein $X_1$ and $X_2$ are the same or different and each represents a hydrogen atom, a fluorine atom or a chlorine atom, provided that $X_1$ and $X_2$ are not fluorine atoms simultaneously, and wherein said polymer has at one end a polar group having the formula $$-COF$$

and at the other end a fluorine atom or a group of the formula $C_qF_{2q+1}O-$ wherein q is an integer of 1 to 15; and wherein said polymer has molecular weight in the range of 500 to 200,000.

2. The termiticide according to claim 1, wherein said polymer is a polymer of the formula:

$$X-(C_3F_6O)_l-(C_2F_4O)_m-(CF_2O)_n-(C_2F_4)_p-Y \quad (I)$$

wherein X is a fluorine atom or a group of the formula: $C_qF_{2q+1}O-$ in which q is an integer of 1 to 15; Y is a group of the formula: $-COF$; l is a number of from 0 to 200; m is a number of from 0 to 200, n is a number of from 0 to 200; and p is a number of from 0 to 200, provided that the sum of l, m and n is not zero.

3. The termiticide according to claim 1, wherein said polymer is a polymer of the formula:

$$X-(CX_1X_2CF_2CF_2O)_r-(CX_1X_2CF_2)_n-Y \quad (II)$$

wherein $X_1$ and $X_2$ are the same as defined above, and wherein X is a fluorine atom or a group of the formula: $C_qF_{2q+1}O-$ in which q is an integer or 1 to 15; Y is a group of the formula: $-COF$; n is a number of from 0 to 200, and r is a number of from 1 to 200.

4. A method for controlling termite damage comprising applying an effective amount of a termiticide composition to a material, wherein said composition comprises, as an active ingredient, a polymer which comprises repeating units of the formula:

$$-C_xF_{2x}O-$$

wherein X is an integer of from 1 to 4, or the formula:

$$-CX_1X_2CF_2CF_2O-$$

wherein $X_1$ and $X_2$ are the same or different and each represents a hydrogen atom, a fluorine atom or a chlorine atom, provided that $X_1$ and $X_2$ are not fluorine atoms simultaneously, and wherein said polymer has at one end a polar group of the formula —COF and at the other end a fluorine atom or a group of the formula $C_qF_{2q+1}O$— wherein q is an integer of 1 to 15; wherein said polymer has molecular weight in the range of 500 to 200,000.

5. The method according to claim 4, wherein said polymer is a polymer of the formula:

$$X-(C_3F_6O)_l-(C_2F_4O)_m-(CF_2O)_n-(C_2F_4)_p-Y \quad (I)$$

wherein X is a fluorine atom or a group of the formula: $C_qF_{2q+1}O$— in which q is an integer of 1 to 15; Y is a group of the formula: —COF; and R' is a halogen atom; l is a number of from 0 to 200; m is a number of from 0 to 200, n is a number of from 0 to 200; and p is a number of from 0 to 200, provided that the sum of l, m and n is not zero.

6. The method according to claim 4, wherein said polymer is a polymer of the formula:

$$X-(CX_1X_2CF_2CF_2O)_r-(CX_1X_2CF_2)_n-Y \quad (II)$$

wherein $X_1$ and $X_2$ are the same as defined above, and wherein X is a fluorine atom or a group of the formula: $C_qF_{2q+1}O$— in which q is an integer or 1 to 15; Y is a group of the formula: —COF; n is a number of from 0 to 200, and r is a number of from 1 to 200.

7. The termiticide composition according to claim 1, wherein said composition further comprises an organic solvent.

8. The termiticide composition according to claim 1, wherein said composition is in the form of an emulsion and further comprises an emulsifier.

9. The termiticide composition according to claim 1, wherein said composition further comprises an ant-controlling amount of an organic phosphorus base insecticide.

10. The termiticide composition according to claim 5, wherein Y is represented by the —COR group.

11. A composition for protecting materials from termite damage comprising an organic solvent and a polymer represented by the formula:

$$X-(C_3F_6O)_l-(C_2F_4O)_m-(CF_2O)_n-(C_2F_4)_p-Y$$

wherein X represents a fluorine atom or a group of the formula $C_qF_{2q+1}O$— in which q is an integer of from 1 to 15; Y is represented by the group —COF; l is a number of from 0 to 200, m is a number of from 0 to 200, n is a number of from 0 to 200, and p is a number of from 0 to 200, provided that the sum of l, m and n is not zero; wherein said polymer is contained in an amount of from 0.1 to 20% by weight based on the total weight of the composition.

12. The composition according to claim 11, wherein said organic solvent is selected from the group consisting of trichlorotrifluoroethane, pentafluorodichloropropane, hexafluorotetrachlorobutane, perfluorohexane, tetrahydrofuran diglyme, triglyme, and tetraglyme.

13. The composition according to claim 11, wherein said composition further comprises an antiseptic agent or an ant-controlling agent.

* * * * *